US005733915A

United States Patent [19]

Sandborn

[11] Patent Number: 5,733,915
[45] Date of Patent: Mar. 31, 1998

[54] USE OF AZATHIOPRINE TO TREAT CROHN'S DISEASE

[75] Inventor: William J. Sandborn, Rochester, Minn.

[73] Assignee: Glaxo Wellcome Inc., Research Triangle Park, N.C.

[21] Appl. No.: 413,783

[22] Filed: Mar. 30, 1995

[51] Int. Cl.$^6$ .......................... A61K 31/52; A61K 31/415
[52] U.S. Cl. .......................... 514/262; 514/391; 514/395
[58] Field of Search .......................... 514/391, 395, 514/262

[56] References Cited

U.S. PATENT DOCUMENTS 3,056,785  10/1962  Hitchings et al. .......................... 260/252

OTHER PUBLICATIONS

P.C. Adamson et al., "A phase II trial of continuous–infusion 6–mercaptopurine for childhood solid tumors", *Cancer Chemother. Pharmacol.*, 26, 343–344 (1990).

C.A.S. Arndt et al., "Bioavailability of low–dose vs. high–dose 6–mercaptopurine", *Clin. Pharmacol. Ther.*, 43, 588–591 (May 1988).

G.L.C. Chan et al., "Azathioprine Metabolism: Pharmacokinetics of 6–Mercaptopurine, 6–Thiouric Acid and 6–Thioguanine Mucleotides in Renal Transplant Patients", *J. Clin. Pharmacol.*, 30, 358–363 (1990).

W.R. Connell et al., "Bone Marrow Toxicity caused by azathioprine in inflammatory bowel disease: 27 years of experience", *Gut*, 34, 1081–1085 (1993).

A.B. Hawthorne et al., "Randomised controlled trial of azathioprine withdrawal in ulcerated colitis", *Brit. J. Med.*, 305, 20–22 (1992).

M. Klein et al., "Treatment of Crohn's Disease with Azathioprine: A Controlled Evaulation", *Gastroenterology*, 66, 916–922 (1974).

B.I. Korelitz et al., "Shortcomings of the National Crohn's Disease Study: The Exclusion of Azathioprine Without Adequate Trial", *Gastroenterology*, 80, 193–194 (1981).

B.I. Korelitz et al., "Favorable Effect of 6–Mercaptopurine on Fistulae of Crohn's Disease", *Digestive Diseases and Sciences*, 30, 58–64 (Jan. 1985).

L. Lennard et al., "Azathioprine metabolims in kidney transplant recipients", *Br. J. Clin. Pharmac.*, 18, 693–700 (1984).

J. Markowitz et al., "Long–Term 6–Mercaptopurine Treatment in Adolescents with Crohn's Disease", *Gastroenterology*, 99, 1347–1351 (1990).

M. Nyman et al., "Long–Term Immunosuppressive Treatment in Crohn's Disease", *Canadian J. Gastroenterology*, 20, 1197–1203 (Nov. 10, 1985).

B. Odlind et al., "Serum Azathioprine and 6–Mercaptopurine Levels and Immunosuppressive Acitivity after Azathioprine in Uremic Patients", *Int. J. Immunopharmac.*, 8, 1–11 (1986).

D.P. O'Donoghue et al., "Double–Blind Withdrawal Trial of Azathioprine as Maintenance Treatment for Crohn's Disease", *The Lancet*, 955–957 (Nov. 4, 1978).

J. Perrault et al., "6–Mercaptopurine Therapy in Selected Cases of Corticosteroid–Dependent Crohn's Disease", *Mayo Clin. Proc.*, 66, 480–484 (1994).

D.H. Present et al., "Treatment of Crohn's Disease with 6–Mercaptopurine", *N. Eng. J. Med.*, 302, 981–987 (May 1, 1980).

D.H. Present et al., "6–Mercaptopurine in the Management of inflammatory Bowel Disease Short– and Long– Term Toxicity", *Annals of Internal Medicine*, 111, 641–649 (Oct. 15, 1989).

J. Rhodes et al., "Controlled Trial of Azathioprine in Crohn's Disease", *The Lancet*, 1273–1276 (Dec. 11, 1971).

J.L. Rosenberg et al., "A Controlled Trial of Azathioprine in Crohn's Disease", *Digestive Diseases*, 20, 721–726 (Aug. 1975).

J.W. Singleton, "Azathioprine Has a Very Limited Role in the Treatment of Crohn's Disease", *Digestive Diseases and Sciences*, 26, 368–371 (Apr. 1981).

R.W. Summers et al., "National Cooperative Crohn's Disease Study: Results of Drug Treatment", *Gastroenterology*, 77, 847–869 (1979).

M. Verhave et al., "Azathioprine in the treatment of children with inflammatory bowel disease", *J. Pediatrics*, 117, 809–814 (Nov. 1990).

J.M.T. Willoughby et al., "Controlled Trial of Azathioprine in Crohn's Disease", *The Lancet*, 944–946 (Oct. 30, 1971).

W.P. Wilson et al., "Azathioprine" in *Analytical Profiles of Drug Substances*, vol. 10; K. Florey, Ed.; Academic Press: New York; pp. 30–53; 1981.

S. Zimm et al., "Phase I and Clinical Pharmacological Study of Mercaptopurine Administered as Prolonged Intravenous Infusion", *Cancer Research*, 45, 1869–1873 (Apr. 1985).

S. Zimm et al., "Variable Bioavailability of Oral Mercaptopurine", *N. Eng. J. Med.*, 308, 1005–1009 (1983).

*Primary Examiner*—Theodore J. Criares
*Attorney, Agent, or Firm*—Robert T. Hrubiec; Warren D. Woessner

[57] ABSTRACT

A therapeutic method for the treatment of Crohn's disease is provided, comprising administering to a patient in need of said treatment an intravenous dose of azathioprine or a pharmaceutically acceptable derivative thereof.

14 Claims, 4 Drawing Sheets

USE OF AZATHIOPRINE TO TREAT CROHN'S DISEASE

STATEMENT OF GOVERNMENT RIGHTS

The present invention was made with the support of the United States Government via grants from the United States Public Health Service (Grant RR-00585). The government has certain rights in the invention.

BACKGROUND OF THE INVENTION

Crohn's disease is a chronic inflammatory condition of unknown etiology which may involve the small bowel, the colon, or both. Subgroups of patients may have predominantly active inflammatory disease, fistulous disease, or strictures. The standard therapy for Crohn's disease includes sulfasalazine, corticosteroids, and mesalamine which are effective as initial treatment in 60 to 80 percent of patients. Nonresponders often undergo surgical resection which may be followed by recurrence which again may be refractory to medical therapy. In addition, some patients who initially respond later relapse and become steroid dependent or require surgical resection. Patients with fistulous Crohn's disease can be even more difficult to manage, and the mainstay medical therapy is metronidazole. At the present time, active inflammatory Crohn's disease which is refractory to standard medical therapy and fistulous Crohn's disease which is refractory to metronidazole are often treated with azathioprine (AZA) or its metabolite 6-mercaptopurine (6-MP).

Controlled trials performed in the 1970's with orally administered 6-MP and AZA in patients with Crohn's disease showed conflicting results. Thus, the role of these agents in the treatment of such inflammatory bowel disorders became controversial. In 1980, Present and colleagues reported that orally administered 6-MP was effective in the treatment of Crohn's disease in a long-term, double-blind, placebo-controlled trial (Present et al., *N. Eng. J. Med.*, 302, 981 (1980)). The mean time to response in this study was three months. The authors hypothesized that the negative outcomes of some of the previous trials were related to inadequate duration of treatment (Korelitz et al., *Gastroent.*, 80, 193 (1981)). Multiple subsequent studies have demonstrated that orally administered 6-MP and AZA are useful in patients with Crohn's disease with refractive active disease, steroid dependent disease, and fistulous disease. However, the utility of these drugs continues to be limited by a slow onset of action when administered orally (3.1 months for Crohn's disease), failure to respond in 35% of patients, and toxicity.

AZA and 6-MP are prodrugs whose metabolites have both cytotoxic and immunosuppressive activity. After absorption, AZA is rapidly and completely converted to 6-MP by a non-enzymatic mechanism. Enzymes which metabolize 6-MP are present in intestinal mucosa as well as in the liver and result in extensive first and second pass metabolism of AZA and 6-MP. These factors are felt to explain, at least in part, the poor bioavailability of 6-MP and AZA, 16% (range 15–37%) and 18% (range 2–72%), respectively (Zinn et al., *N. Eng. J. Med.*, 308, 1005 (1983); Odlind et al., *Int. J. Immuno. Pharmac.*, 8, 1 (1986)). One of the metabolites of 6-MP, 6-thioguanine nucleotide (6-TGN), is thought to be the metabolite with immunosuppressive activity.

The half-lives of 6-TGN's parent compounds, AZA and 6-MP, are very short, ranging from one to two hours. In contrast, the half life of 6-TGN in red blood cells (RBCs) appears to be at least three days. The time required to reach steady state levels of 6-TGN in RBCs varies, with studies showing ranges of 4 to 28 days and 4.5 months to greater than 3 years. In all of these studies, there were patients at the end of the monitoring period who still had not reached steady state levels of 6-TGN in their RBCs. All of the studies discussed above used low to moderate doses of orally administered 6-MP or AZA: 50–75 mg/m$^2$/d; or 1–3 mg/kg/d.

Zimm et al. (*Cancer Res.*, 45, 1869 (1985)) reported the treatment of patients with refractory hematologic and solid tumor malignancies with high doses of 6-MP. The patients received continuous IV infusion of 6-MP at 50 mg/m$^2$/hr in 12 hour increments ranging from 12 hours up through 60 hours. RBC 6-TGN concentrations gradually rose over the course of the infusion to a mean of 870±188 pg/8×10$^8$ RBCs. After the infusion was discontinued, RBC 6-TGN concentrations remained elevated for a few days, consistent with the known long half life of this compound as discussed above. A subsequent study found that continuous infusion of 6-MP at a dose of 50 mg/m$^2$/hr was well tolerated (Adamson et al., *Cancer Chemother. Pharmacol.*, 26, 343 (1990)). However, neither study found that intravenous administration of 6-MP elicited a therapeutic response in patients with refractory hematologic and solid tumor malignancies.

Thus, there is a continuing need to administer a therapeutic yet non-toxic dose of AZA or 6-MP, or pharmaceutically acceptable salts thereof, in a manner that accelerates the onset of the immunosuppressive action of AZA or 6-MP.

SUMMARY OF THE INVENTION

The present invention provides a therapeutic method comprising administering to a human patient in need of immunosuppression, such as a patient afflicted with Crohn's disease or another immunoregulatory disorder, a continuous intravenous infusion of azathioprine (AZA), 6-MP, or a pharmaceutically acceptable salt thereof, at a dosing rate effective to substantially accelerate the onset of the immunosuppressive action of azathioprine, 6-MP, or a pharmaceutically acceptable salt thereof, in said patient. A dose of about 1500–5900 mg of azathioprine is administered to an adult patient over a period of about 30–40 hours via a continuous intravenous infusion. This is a rate of about 35–200 mg/hour. For example, in the working example presented hereinbelow, the dosing rate for intravenous administration of azathioprine is 50 mg/hr for a total of 1800 mg over 36 hours. The azathioprine, 6-MP, or a pharmaceutically acceptable salt thereof, is preferably administered in combination with a pharmaceutically acceptable liquid carrier.

A preferred embodiment of the invention comprises the intravenous administration of azathioprine followed by oral administration of azathioprine at 1–2.5 mg/kg/day, for at least 16 weeks, up to periods of time of about 1–2 years. 6-Thioguanine nucleotide concentrations in red blood cells are preferably about 50–400 pmol/10$^8$ red blood cells after intravenous therapy is completed and preferably maintained at a level of about 50–500 pmol/10$^8$ red blood cells for at least 4 months after intravenous therapy, while the patient is taking azathioprine orally. The 6-methylmercaptopurine concentration in red blood cells is preferably about 1000–7000 pmol/10$^8$ red blood cells after intravenous therapy is completed.

Patients in need of immunosuppression which are amenable to treatment by the present method include, but are not limited to, patients afflicted with rheumatoid arthritis, ulcerative colitis, Crohn's disease, or patients who are undergoing or have undergone an organ transplant.

For example, a human patient to be treated with azathioprine, 6-MP, or a pharmaceutically acceptable salt thereof, may be afflicted with active inflammatory Crohn's disease, Crohn's fistulous disease, or steroid dependent Crohn's disease, any of which may be refractory to standard medical therapy. Patients can be selected who exhibit a Crohn's Disease Activity Index (CDAI) before continuous intravenous azathioprine therapy of about 250, or more. As used herein, the term "substantially accelerate" is defined as reducing a patient's CDAI by at least 100 points in less than about one month following the completion of continuous intravenous azathioprine therapy. The CDAI score can be decreased by a reduction in either or both the number or severity of symptoms, based on objective or subjective criteria, as discussed hereinbelow. In contrast, the oral administration of azathioprine at 1–2.5 mg/kg/day for about three to four months is required to achieve a similarly significant therapeutic effect. Thus, oral administration of AZA is not effective to treat outbreaks of active inflammatory Crohn's disease, since the onset of action is so slow.

DETAILED DESCRIPTION OF THE INVENTION

Figure 1:
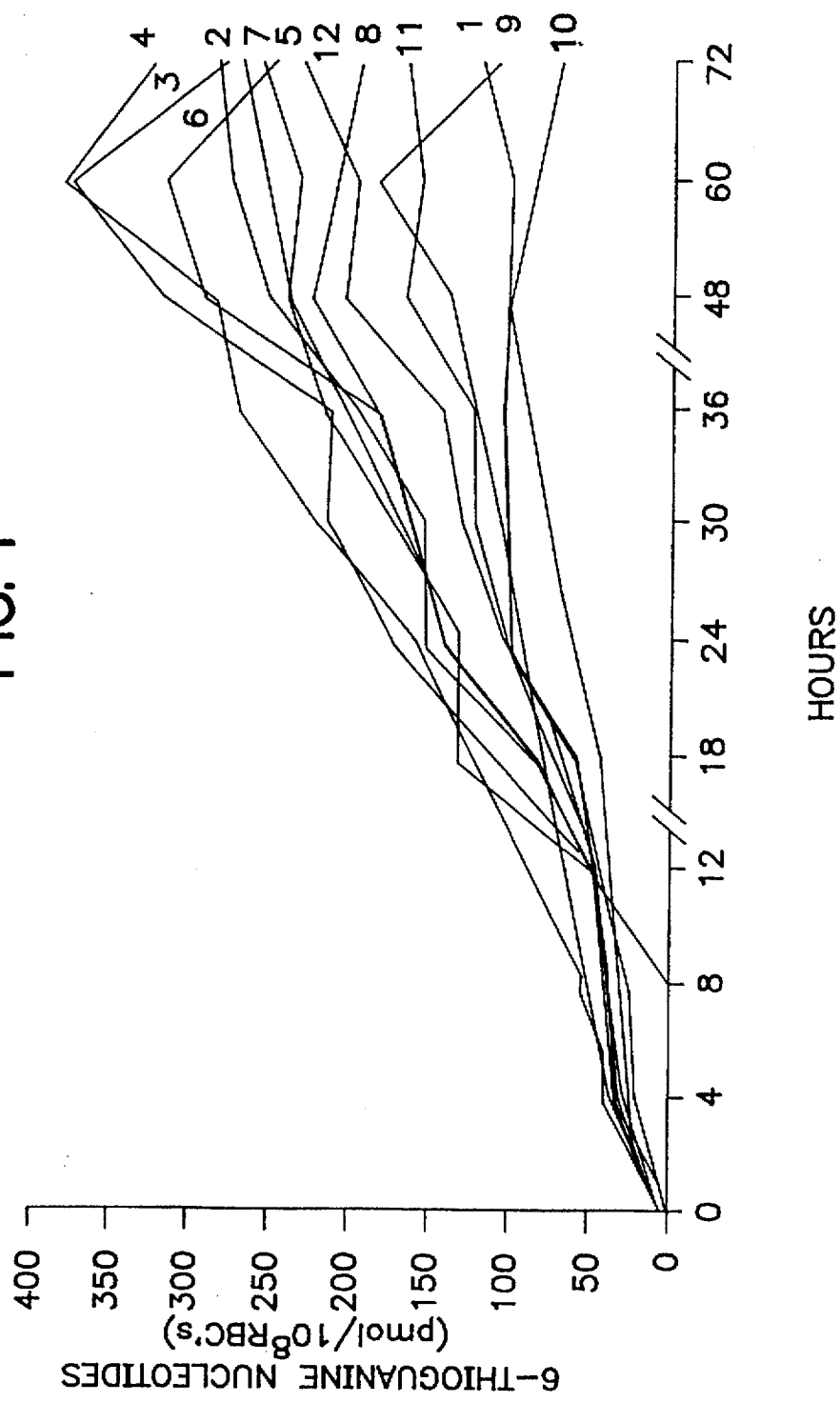
FIG. 1. Erythrocyte 6-thioguanine nucleotide (6-TGN) concentrations during AZA IV loading in twelve patients with Crohn's disease.

It will be further appreciated that the amount of AZA or 6-MP required for use in treatment will vary not only with the particular form of AZA or 6-MP but also with the severity of the symptoms being treated and the age and condition of the patient. The goal of treatment is to obtain a dosing rate effective to substantially accelerate the onset of the immunosuppressive action of azathioprine in said patient, over that achievable by conventional oral dosing of AZA, i.e., 1–2.5 mg/kg/day.

The invention further provides a pharmaceutical formulation comprising AZA, 6-MP, or a pharmaceutically acceptable salt thereof, together with one or more pharmaceutically acceptable carriers thereof, and optionally, other therapeutic and/or prophylactic ingredients which are adapted for continuous intravenous infusion. The carriers must be acceptable in the sense that they are compatible with the other ingredients of the formulation and not deleterious to the recipient thereof.

AZA or 6-MP may be delivered as a suspension, solution, or emulsion in oily or aqueous vehicles, and may contain such formulary agents such as suspending, stabilizing and/or dispersing agents. Suitable aqueous vehicles include physiological saline, phosphate-buffered saline, and other vehicles for parenteral drug delivery, generically referred to as "intravenous solutions". Alternatively, the active ingredient may be in powder form, obtained by aseptic isolation of sterile solid or lyophilized from solution, with a suitable vehicle, e.g. sterile, pyrogen-free water, before use. The pharmaceutical compositions according to the invention may also contain other active ingredients such as antimicrobial agents, or preservatives. The compounds of the present invention may also be used in combination with other therapeutic agents and nutritional supplements.

The invention will be further described by reference to the following detailed example.

EXAMPLE

Twelve patients diagnosed with Crohn's disease were recruited to study the therapeutic effect of AZA intravenous (IV) dosing for 36 hours followed by four months of oral administration of AZA. Patients recruited for the study fell into one of two groups. One group had Crohn's ileitis, colitis or ileocolitis: an inflammatory process with involvement of the terminal portion of the ileum plus at least a portion of the colon, or involvement of the colon, or a portion thereof, which has the typical appearance of Crohn's disease as diagnosed by small bowel barium X-ray and colonoscopy. The other group exhibited Crohn's perianal, enterocutaneous or enterovaginal fistulous disease: an inflammatory/fistulous process which may connect the small bowel or colon with the skin of the vagina or involve the perianal region and which has the typical appearance of Crohn's fistulous disease as diagnosed by colonoscopy, colon x-ray, small bowel barium x-ray, or fistulogram.

To participate in this study, patients with inflammatory Crohn's disease were either refractory to high-dose intravenous corticosteroid therapy or were corticosteroid intolerant. Corticosteroid therapy was continued during the study until an improvement in Crohn's disease was documented, then corticosteroid treatment was tapered off. Other concomitant medications were unchanged throughout the study.

Patients with fistulous Crohn's disease previously failed a trial of metrorddazole at a dose of at least 750 mg/day for greater than 2 months or had a history of adverse effects during metronidazole therapy. If patients were on metronidazole therapy at the beginning of the study, they continued at the entry level dose until improvement was documented. Once improvement was documented, metronidazole therapy was discontinued. Other concomitant medications were unchanged throughout the study.

Patients who had used AZA, 6-MP, cyclosporine, or methotrexate in the previous 6 months were excluded from the study.

Six of the patients had moderate to severe active inflammatory Crohn's disease with a Crohn's Disease Activity Index (CDAI) score of at least 250 and the other six had fistulous Crohn's disease with a total of 13 fistula.

At the beginning of the study, patients were evaluated to determine a baseline CDAI score (Table 1). The CDAI was developed for the National Cooperative Crohn's Disease Study (Best et al., Gastroent., 70, 339 (1976); Best et al., Gastroent., 77, 843 (1979)). The index incorporates both subjective (patient symptoms) and objective (physical exam, laboratory tests) data and is an index of disease severity. The CDAI for each patient was calculated from the laboratory data which was obtained at the time of initial visit, at the time of the 4 week, 8 week, and 16 week follow-up visits; and from the diary sheets for the initial 7 days before starting AZA and from the diary sheets for the 7-day period preceding the week 4, week 8, and week 16 follow-up visits.

Complete success, i.e., clinical remission, was defined as a CDAI score of <150 points. Partial success, i.e., clinical improvement, was defined as a reduction in the CDAI score of $\geq 100$ points. A secondary determinant of response was the endoscopic appearance of the colon as determined by serial flexible sigmoidoscopy at entry, and after week 4, week 8, and week 16. Endoscopic improvement was defined as a decrease in the endoscopic findings of inflammation with the presence of only patchy superficial ulceration and erythema of the mucosa. Endoscopic remission was defined as either normal appearing mucosa; or scarring or pseudopolyps without any endoscopic evidence of active inflammation.

Other indices of disease severity which can be employed in evaluating the efficacy of the presently claimed method are the SICDA (Simple Index of Crohn's Disease Activity), SCCPACD (Simplified Clinical Classification of Perianal Crohn's Disease) for perianal Crohn's disease, or the therapeutic goal scoring system, a clinical grading scale for fistulous Crohn's disease (Harvey et al., *Lancet*, 1, 514 (1980); Hughes et al., *EIS:Rectum*, 35, 928 (1992); (Present et al., *N. Eng. J. Med.*, 302, 981 (1980); Korelitz, *Gastroent.*, 80, 193 (1985); Brynskov et al., *N. Eng. J. Med.*, 321, 845 (1989)).

Seven days after beginning the study, patients were admitted to the General Clinical Research Center at St. Mary's Hospital. During the first 36 hours of the admission, patients received a continuous IV infusion of AZA at a dose of about 50 mg per hour for a total IV loading dose of 1800 mg per patient. 5 ml blood samples were obtained at 0, 4, 8, 12, 18, 24, and 36 hours during the infusion. After termination of the infusion, the patients were monitored in the hospital for an additional 36 hours during which time serial blood samples were obtained to complete the pharmacokinetic study. Seventy-two hours after entering the hospital, patients began receiving orally administered AZA at 50–100 mg/day. If no clinical response was observed after 4–8 weeks and no adverse events had occurred, the oral dose of AZA was increased to 100–150 mg/day. 5 ml blood samples were obtained just before the daily oral dose at week 2, 4, 6, 8, 10, 12, 14, and 16. The patients returned for follow-up visits at week 4, week 8 and week 16.

TABLE 1

| Variable | | Weighing Factor |
|---|---|---|
| $X_1$ | Number of liquid or very soft stools in one week. | 2 |
| $X_2$ | Sum of 7 daily abdominal pain ratings (0 = none, 1 = mild, 2 = moderate, 3 = very poor, 4 = terrible). | 5 |
| $X_3$ | Sum of 7 daily ratings of general well being (0 = generally well, 1 = slightly below par, 2 = poor, 3 = very poor, 4 = terrible). | 7 |
| $X_4$ | Total number of the following symptoms or findings present during the week: (1) arthritis or arthralgia (2) skin or mouth lesions (e.g., pyoderma gangrenosum, erythema nodosum, aphthous stomatitis) (3) iritis or uveitis (4) anal fissure, fistula, or perirectal abscess (5) other external fistula (e.g., enterovesical, enterovaginal, enterocutaneous) (6) febrile episode exceeding 100° F. during week | 20 |
| $X_5$ | Taking Imodium or other opiate for diarrhea (0 = no, 1 = yes). | 30 |
| $X_6$ | Abdominal mass (0 = no, 2 = questionable, 5 = definite). | 10 |

TABLE 1-continued

| Variable | | Weighing Factor |
|---|---|---|
| $X_7$ | Anemia (47 minus hematocrit, males; 42 minus hematocrit, females). | 6 |
| $X_8$ | Body weight (100 × [1 minus body weight/ standard weight]).[a] | 1 |

[a]The 1983 Metropolitan Height and Weight Table was used for calculation of body weight ($X_8$ above).

RESULTS

A therapeutic response was determined by the CDAI score and endoscopic examination for inflammatory Crohn's disease (CD), and by physical and x-ray examination, and by diminishment or cessation of fistula drainage for fistulous CD. RBC concentrations of AZA active metabolites, 6-TGN and 6-MeMP, were measured by high performance liquid chromatography (HPLC).

4/6 patients with inflammatory CD went into remission (2 by week 4, 1 by week 8, 1 by week 16,) and 1/6 temporarily improved by week 4 but underwent colectomy at week 8. 1/6 patients failed and had a colectomy after week 1. All 4 patients who went into remission had endoscopic improvement and 3 of the 4 had complete endoscopic healing. The response was rapid (usually within 1 week) as demonstrated by a reduction in the CDAI score of $\geq 100$ points and endoscopic improvement was evident at week 4 in the majority of patients who responded (Table 2). The rapidity of response was also demonstrated by a reduction in the mean (±SD) CDAI score for responders from 396±93 at baseline to 182±83 by week 4, p<0.01. Thus, the overall response rate was 84%, with a sustained response in 67% of the patients with inflammatory CD.

TABLE 2

CLINICAL AND ENDOSCOPIC RESPONSE IN 6 PATIENTS WITH INFLAMMATORY CROHN'S DISEASE

| | CDAI Score | | | | Endoscopic Appearance | | | |
|---|---|---|---|---|---|---|---|---|
| Patient | Baseline | Week 4 | Week 8 | Week 16 | Baseline | Week 4 | Week 8 | Week 16 |
| 7 | 473 | 256 | 349 | Op[a] | Severe | Severe | Severe[b] | Op[a] |
| 8 | 511 | 612[c] | Op[d] | Op[d] | Severe | Severe[b] | Op[d] | Op[d] |
| 9 | 502 | 101 | 146 | 140 | Moderate | Remission | Remission | Remission |
| 10 | 282 | 84 | 73 | 57 | Severe | Mild | Mild | Remission |
| 11 | 392 | 230 | 198 | 140 | Severe | Mild | Mild | Mild |
| 12 | 331 | 240 | 141 | 145 | Severe | Mild | Remission | Remission |

Op[a]: Indicates operation after week 8.
[b]: Indicates severe gross pathologic appearance.
[c]: Indicates week 1 rather than week 4.
Op[d]: Indicates operation after week 1.

7/13 fistulae closed by week 4 (vaginal=1, enteric=2, perianal=2, severely edematous tags=2) and 3/13 fistulae had a temporary decrease in drainage (cutaneous=2, bladder=1) (Table 3) in fistulous CD patients. 2/13 failed to improve (vaginal=1, watering pot=1). One fistula improved at week 16 (watering pot=1). Four patients were operated: watering pot=1, cutaneous =1, cutaneous/bladder=1 at week 4, and vaginal=1 at week 8. Therefore, the overall response rate in patients with fistulous disease was 85%, with a sustained response rate of 62%.

CD, the RBC 6-TGN concentrations were somewhat higher in the 5 patients who had improvement at least one fistula site than in the single patient who had no improvement.

Moreover, the mean (±SD) steroid doses of patients during the study were decreased during the 16 week study period (Table 4). 6/8 patients receiving prednisone reduced the dose to 5 mg/d or less by week 16, and the mean prednisone dose was reduced from 33 mg/d to 9 mg/d. The mean steroid dose at baseline, week 4, week 8, and week 16 were 33±24, 24±17, 14±17, and 9±17, respectively, with the

TABLE 3

FISTULA RESPONSE IN 6 PATIENTS WITH FISTULIZING CROHN'S DISEASE

| Patient | Fistula Type | Response to Treatment | | |
|---|---|---|---|---|
| | | Week 4 | Week 8 | Week 16 |
| 1 | Watering Pot Perineum | No change | No change | Op[a] |
| 2 | Perianal (4 fistulae) | Improved 4/4 | Healed 3/4 Improved 1/4 | Healed 4/4 |
| 3 | Rectovaginal | No change | No change | No change[b] |
| | Edematous Anal Tags | Healed | Healed | Healed |
| 4 | Rectovaginal | Healed | Healed | Op[a] |
| | Enterocutaneous | Temporary Improvement | Recurrent Drainage | Op[a] |
| | Enteroenteric | Healed | Healed | Op[a] |
| | Edematous Skin Tags | Healed | Healed | Op[a] |
| | Perianal (2 fistulae) | Healed | Healed | Op[a] |
| 5 | Watering Pot Perineum | No change | No change | Improved |
| 6 | Enterocutaneous | Temporary Improvement | Recurrent Drainage | Op[a] |
| | Enteroenteric (multiple) | Healed | Healed | Op[a] |
| | Enterovesicle | Temporary Closure | Recurrent Fistula | Op[a] |

Op[a]: Indicates operation after week 8.
[b]: Indicates patients operated for persistent rectovaginal fistula after week 16.

Figure 2:
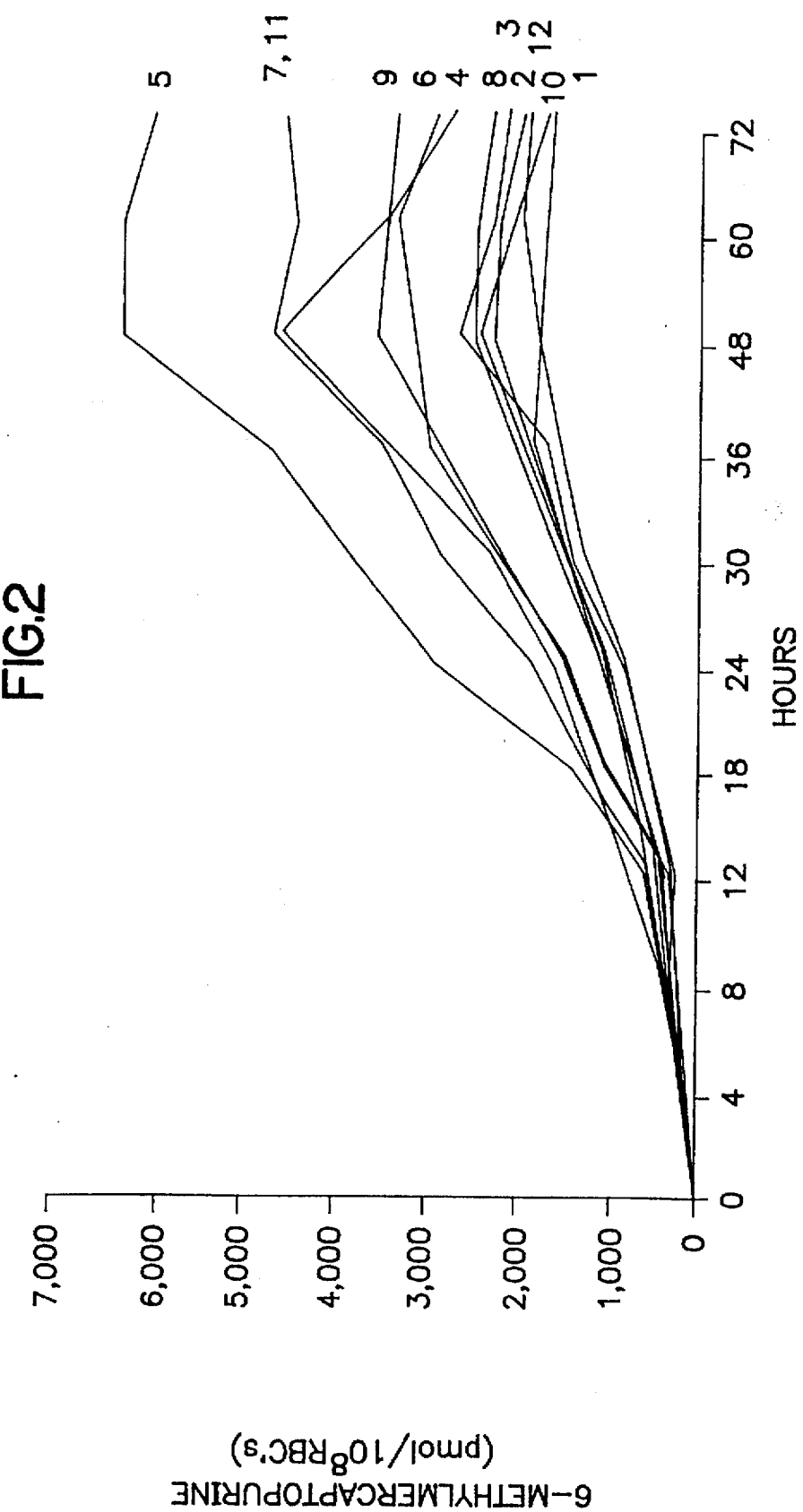
FIG. 2. Erythrocyte 6-methylmercaptopurine (6-MeMP) concentrations during AZA IV loading in Crohn's disease patients.
Figure 3:
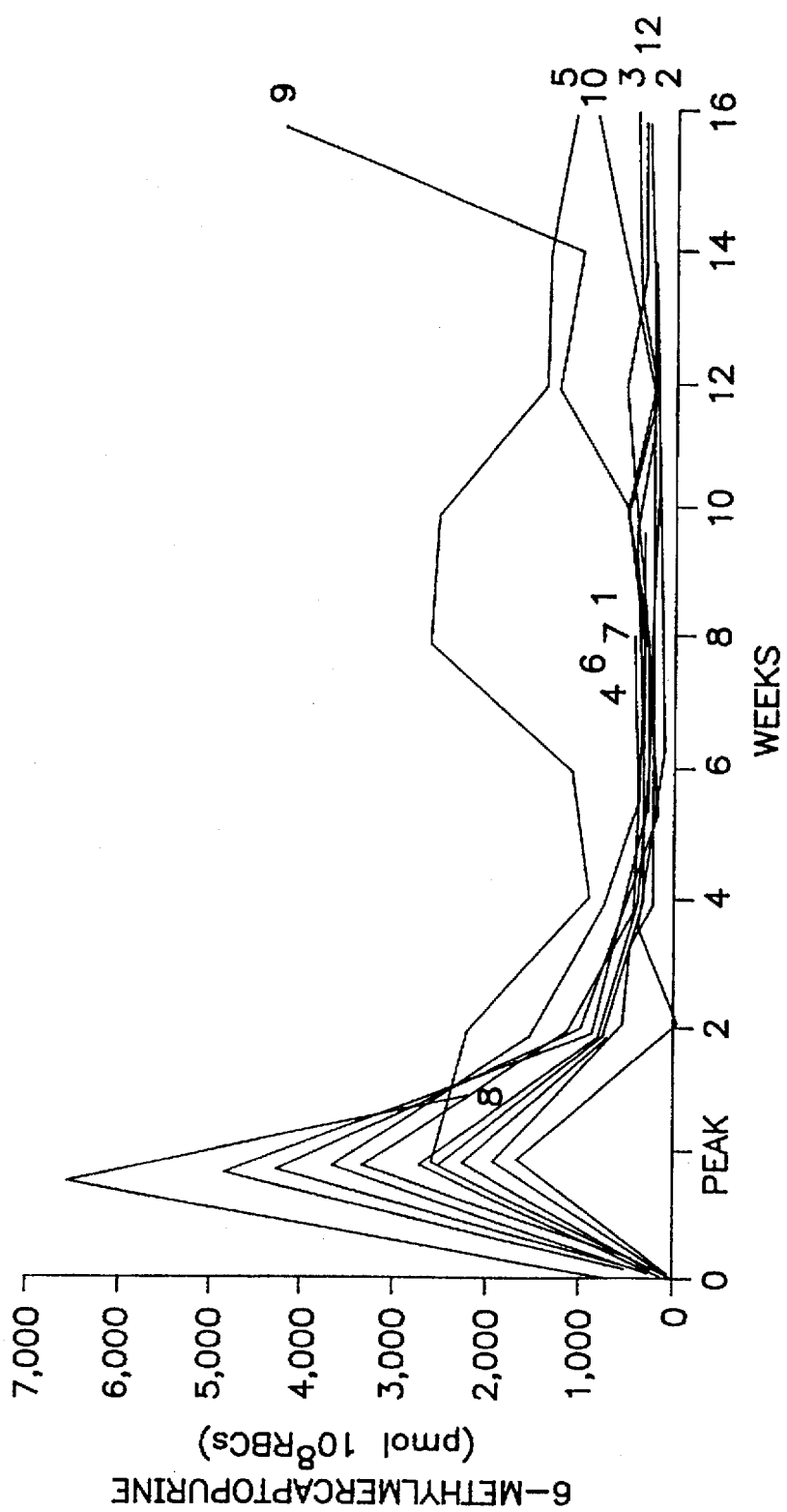
FIG. 3. Erythrocyte 6-TGN concentration following AZA IV loading in Crohn's disease patients.
Figure 4:
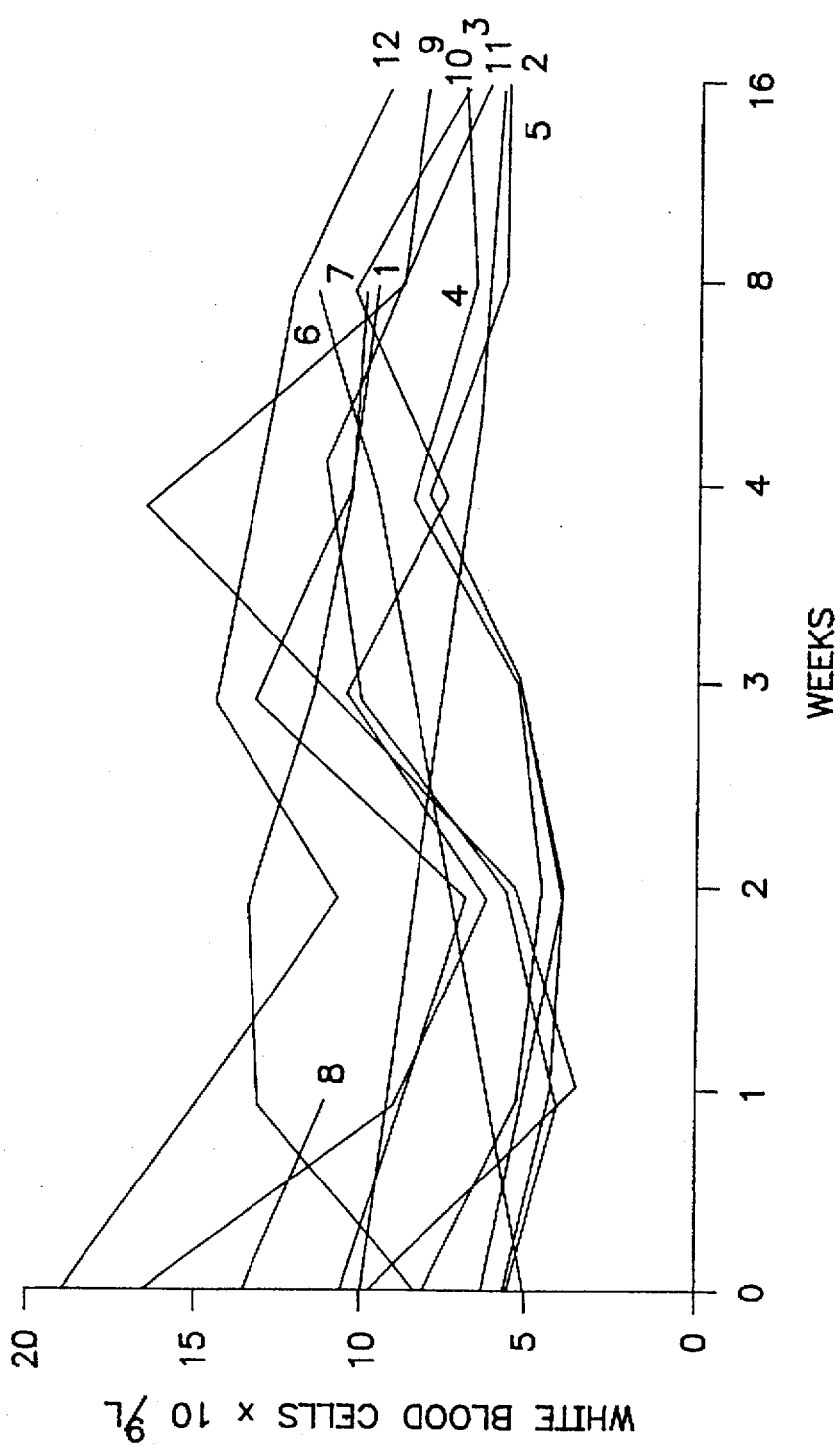
FIG. 4. Erythrocyte 6-MeMP concentrations following AZA IV loading in Crohn's disease patients.

The respective mean 6-TGN and 6-MeMP concentrations following the IV loading dose and at weeks 4, 8, and 16 were: 241±91, 132±76, 140±64, and 174±83 pmol/$10^8$ RBC; and 3402±1488, 263±198, 318±716, and 853±1319 pmol/$10^8$ RBCs. The RBC 6-TGN and 6-MeMP concentrations for each of the 12 patients during the 36 hour infusion and 36 hour post-infusion observation period are shown in FIGS. 1 and 2. The RBC 6-TGN and 6-MeMMP concentrations for each of the 12 patients during the 16 weeks of oral AZA therapy are shown in FIGS. 3 and 4.

Clinical response did not correlate with 6-TGN or 6-MeMP concentrations at the AZA dose studied. Peak concentrations of AZA metabolites occurred within 3 days of the initiation of IV AZA. However, the mean 6-TGN concentration was less than those reported to be efficacious in leukemia (275 pmol/$10^8$ RBC's) or to cause leukopenia (1,000 pmol/$10^8$ RBC's). No toxicity occurred. Moreover, the pharmacokinetic data showed that the RBC concentration of 6-TGN reached a steady state by the end of the 36 hour IV loading dose infusion.

For patients with inflammatory CD, there were no significant correlations between: change in CDAI (baseline to week 4) and both peak and week 4 RBC 6-TGN or 6-MeMP concentrations; change in CDAI (baseline to week 8) and week 8 RBC 6-TGN or 6-MeMP concentrations; and change in CDAI (baseline to week 16) and week 16 RBC 6-TGN or 6-MeMP concentrations. For the patients with fistulizing comparison between baseline and week 16 being significant at p+0.04 (Student's T-test).

TABLE 4

STEROID DOSE REDUCTION IN 8 PATIENTS WITH CROHN'S DISEASE

| | Steroid Dose | | | |
|---|---|---|---|---|
| Patient | Baseline | Week 4 | Week 8 | Week 16 |
| 1 | 10 mg | 10 mg | 0 mg | 0 mg[a] |
| 2 | 10 mg | 5 mg | 2.5 mg | 2.5 mg |
| 6 | 20 mg | 20 mg | 15 mg | 15 mg[a] |
| 8 | 50 mg | 50 mg[b] | 50 mg[b] | 50 mg[b] |
| 9 | 40 mg | 15 mg | 0 mg | 0 mg |
| 10 | 80 mg | 40 mg | 20 mg | 5 mg |
| 11 | 15 mg | 10 mg | 5 mg | 0 mg |
| 12 | 40 mg | 40 mg | 20 mg | 0 mg |
| Mean | 33 mg | 24 mg | 14 mg | 9 mg[c] |
| SD | 24 mg | 17 mg | 17 mg | 17 mg |

[a]: Indicates steroid dose prior to operation at week 8.
[b]: Indicates steroid dose prior to operation at week 1.
[c]: Indicates week 16 is significantly less than baseline, P = 0.04 (Student's T-test).

In summary, patients receiving high doses of AZA administered via continuous intravenous infusion, showed a rapid increase in the levels of 6-TGN in RBCs, concomitant with a rapid improvement in these patients clinical picture.

METHODS

Serum Concentrations of 6-MP and RBC Concentrations of 6-TGN and 6-MeMP

The serum concentrations of 6-MP as well as the RBC concentrations of 6-TGN and 6-MeMP were determined by high performance liquid chromatography (HPLC) as previously described (Chan et al., *J. Clin. Pharmacol.*, 30, 358 (199); Erdmann et al., *J. Liq. Chromato.*, 11, 971 (1988); Erdmann et al., *Biomed. Chromato.*, 4, 47 (1990); Erdmann et al., *J. Chromato.*, 571, 149 (1991)). Blood samples (5 mL) from adult patients were obtained in EDTA containing sodium heparin Vacutainer tubes. Because AZA and 6-MP are rapidly metabolized in whole blood, immediate cooling and freeze centrifugation was required to stop these reactions (Ding et al., *J. Chromato.*, 163, 281 (1979); Odlind et al., *Scand. J. Urol. Nephrol.*, 564, 213 (1981); Floberg et al., *J. Chromato.*, 225, 73 (1981); Liliemark et al., *Ther. Drug Monit.*, 12, 339 (1990)). This involved centrifugation of whole blood at 160 g for 10 minutes at 1° C. The serum was then separated and stored at −70° C. after addition of dithiothreitol, a sulfhydryl group protecting agent. The RBCs were washed twice in two volumes of normal saline and centrifuged first at 160 g (10 minutes, 1° C.) and second at 640 g (10 minutes, 1° C.). Finally, RBCs were diluted one to one with normal saline, counted with a cell counter, and then stored at a concentration of approximately $8 \times 10^8$ cells/200 uL, at −70° C. If only RBC 6-MP and 6-MeMP were assayed, the sample was stable up to 3 days and could be mailed for processing.

The serum 6-MP assay was performed as follows. Serum samples were precipitated with acetonitrile containing 6-n-propyl-2-thiouracil as the internal standard. The chromatographic separation was performed with an octadecyl-silane column with the mobile phase consisting of acetonitrile and 0.01M sodium dihyrogen phosphate at a pH of 6.1. The separation was performed isocratically with the acetonitrile concentration at 16% (v/v). The flow rate was 1.5 mL/minute. The column effluent was monitored at 323 nm for detection of 6-MP.

The assays for RBC 6-TGN and 6-MeMP were performed as follows. The RBCs were thawed and the free base of each thiopurine was liberated from the respective nucleoside and nucleotide moieties by a combination of heat and acid hydrolysis with sulfuric acid. The hydrolysate was further purified by the addition of perchloric acid. To assay 6-thioguanine (which is the parent base of 6-TGN), the following steps were taken. First, an organic extraction was performed by the addition of dichloromethane. Following centrifugation the aqueous layer was removed and oxidized by the addition of sodium bicarbonate and potassium permanganate. Excess permanganate was removed by hydrogen peroxide after 5 minutes. The sample was then centrifuged and 5 uL of the supernatant was injected for HPLC analysis. 6-thioguanine was separated on an octadecylsilane column using acetonitrile and 20 mM sodium phosphate (15:85, v/v), pH 7.5, containing 0.07% tetrabutylammonium chloride as the mobile phase. 6-thloguanine was detected by fluorescent spectrophotometry, with excitation at 280 nm and emission monitored at 410 nm. No suitable internal standard for the 6-thioguanine assay has been found, so concentrations were detected by comparison to simultaneously created standard curves. The standard curve and all patient samples were done in duplicate.

The assay for RBC 6-MeMP assay was performed as follows. The supernatant from acid hydrolysis was alkalinized with sodium bicarbonate and then organically extracted with the addition of ethylacetate containing an internal standard (sulfamethoxazole). The organic layer was transferred and evaporated to dryness under nitrogen. 6-MeMP and sulfamethoxazole were reconstituted in mobile phase and 5 µL was injected for analysis by HPLC. The mobile phase consisted of acetonitrile and 10 mM sodium phosphate (10:90, v/v), pH 5.75. 6-MeMP was separated on a C-8 cyanopropylsilane column and was detected by UV absorbance at 288 nm. Concentrations of 6-MeMP were detected by comparison with peak heights of the internal standard.

Azathioprine

Injectable AZA (Imuran) is produced by the Burroughs Wellcome Company (Research Triangle Park, N.C.). It was supplied as a 100 mg vial which contained the sodium salt of AZA which was equivalent to 100 mg of AZA sterile lyophilized material and sodium hydroxide to adjust the pH. The addition of 10 mL of sterile water resulted in a solution with an AZA concentration of 10 mg/mL and a pH of approximately 9.6. For the purposes of this study, the AZA was administered at a rate of 50 mg/hr for 36 hours as a continuous IV infusion. The AZA to be continuously infused was prepared just before use from three separate batches which were administered sequentially. Each batch was comprised of the contents of 6 of the 100 mg injectable AZA vials, each diluted with 10 mL of sterile water. The resulting 60 mL was diluted with 540 mL of normal saline for a final volume of 600 mL. The solution was then pH adjusted with sodium hydroxide to a pH of 9.6. Each of the three 600 mL solutions were then continuously infused at 50 mL/hr (50 mg/hr) over a 12 hour period in a sequential fashion for a total infusion duration of 36 hours.

The oral form of AZA (Imuran) is available in tablet form from Burroughs Wellcome Company (Research Triangle Park, N.C.). Each scored tablet contains 50 mg of AZA and inactive ingredients including lactose, magnesium stearate, potato starch, povidone, and stearic acid. The oral form of AZA was administered at a dose of at least 50 mg/day for 16 weeks after the completion of the intravenous phase of the study.

Although exemplified by reference to the treatment of Crohn's disease, it is expected that the present administration method will be useful to accelerate the immunosuppressive action of AZA or 6-MP in other settings in which rapid onset of immunosuppressive action is desirable, such as in the treatment of patients prior to, during, or after solid organ transplantation, or in the treatment of other autoimmune disorders, including rheumatoid arthritis, ulcerative colitis, psoriasis, bullous pemphigoid, eczema, dermatomyocytis, polymyositis, Wegener's granulomatosis, pyoderma grangenosum, idiopathic thrombocytopenia purpura, and Behcet's syndrome.

All publications are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A therapeutic method of treating Crohn's disease comprising administering to a human patient afflicted with Crohn's disease that is corticosteroid intolerant a continuous intravenous infusion of azathioprine, 6-MP, or a pharmaceutically acceptable salt thereof, at a dosing rate and for a period effective to substantially accelerate the onset of the immunosuppressive action of azathioprine over the time required for said onset when azathioprine is administered orally.

2. The method of claim 1 wherein an effective amount of azathioprine, 6-MP, or a pharmaceutically acceptable salt thereof, is administered in combination with a pharmaceutically acceptable liquid carrier.

3. The method of claim 1 wherein azathioprine is administered intravenously at about 35–200 mg/hour.

4. The method of claim 1 wherein the intravenous infusion of azathioprine delivers about 1500–5900 mg over a period of about 30–40 hours.

5. The method of claim 4 wherein the 6-thioguanine nucleotide concentration in red blood cells is about 50–400 pmol/$10^8$ red blood cells after intravenous therapy is completed.

6. The method of claim 4 wherein the 6-methylmercaptopurine concentration in red blood cells is about 1000–7000 pmol/$10^8$ red blood cells after intravenous therapy is completed.

7. The method of claim 1 further comprising administering azathioprine orally following intravenous administration.

8. The method of claim 7 wherein the oral dose is 50–100 mg/day.

9. The method of claim 8 wherein the oral dose is administered for at least 4 months.

10. The method of claim 1 wherein the human patient is afflicted with active inflammatory Crohn's disease.

11. The method of claim 1 wherein the human patient is afflicted with Crohn's fistulous disease.

12. The method of claim 1 wherein the human patient is afflicted with steroid dependent Crohn's disease.

13. The method of claim 1 wherein the 6-thioguanine nucleotide concentration in red blood cells is maintained at a level of about 50–500 pmol/$10^8$ red blood cells for at least 4 months following intravenous therapy.

14. The method of claim 1 wherein the human patient is afflicted with active inflammatory Crohn's disease and the Crohn's Disease Activity Index (CDAI) score of that patient before intravenous azathioprine therapy is $\geq 250$.

* * * * *